United States Patent
Martinez et al.

(10) Patent No.: US 7,321,070 B2
(45) Date of Patent: Jan. 22, 2008

(54) SYNTHESIS OF ISOTOPICALLY LABELED R- OR S-[$^{13}$C, $^2$H] GLYCEROLS

(75) Inventors: Rodolfo A. Martinez, Santa Fe, NM (US); Clifford J. Unkefer, Los Alamos, NM (US); Marc A. Alvarez, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 597 days.

(21) Appl. No.: 10/629,982

(22) Filed: Jul. 30, 2003

(65) Prior Publication Data

US 2005/0027146 A1   Feb. 3, 2005

(51) Int. Cl.
*C07C 31/22* (2006.01)

(52) U.S. Cl. ............... 568/852; 568/853; 568/868; 568/869

(58) Field of Classification Search ............... None
See application file for complete search history.

(56) References Cited

OTHER PUBLICATIONS

Aldrich catalog 1992-1993.*
McLafferty "Interpretation of Mass Spectra", W. A. Benjamin, INC., 1966.*
Pitlik et al., Journal of labeled Compounds and Radiopharmaceuticals, 1997, vol. XXXIX, No. 12, pp. 999-1009.*
Cho et al., Journal of Organic Chemistry, 1993, 58, 7925-7928.*
Matteson et al., "Synthesis of Asymmetrically Deuterated Glycerol and Dibenzylglyceraldehyde Via Boronic Esters," J. Am. Chem. Soc. 1990, 112, 3964-3969.
Nieschalk et al., "A Short Synthesis of (1S,2R)- and (1R,2R)-[1-$^2$H]-Glycerols," Asymmetry, vol. 8, No. 14, pp. 2325-2330, 1997.
Siskos et al., "A Highly Efficient Synthesis of [1-$^{13}$C, $^{18}$O]- and [1-$_{13}$C, $^2$H$_2$]-Glycerol for the Elucidation of Biosynthetic Pathways," Tetrahedron Letters 44 (2003) 789-792.

* cited by examiner

*Primary Examiner*—Yvonne Eyler
*Assistant Examiner*—Valenrod Yevgeny
(74) *Attorney, Agent, or Firm*—Bruce H. Cottrell

(57) ABSTRACT

The present invention is directed to asymmetric chiral labeled glycerols including at least one chiral atom, from one to two $^{13}$C atoms and from zero to four deuterium atoms bonded directly to a carbon atom, e.g., (2S) [1,2-$^{13}$C$_2$] glycerol and (2R) [1,2-$^{13}$C$_2$]glycerol, and to the use of such chiral glycerols in the preparation of labeled amino acids.

15 Claims, No Drawings

SYNTHESIS OF ISOTOPICALLY LABELED R- OR S-[$^{13}$C, $^2$H] GLYCEROLS

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to isotopically labeled compounds and more particularly to stereospecifically labeled glycerol labeled with carbon-13 ($^{13}$C) or with $^{13}$C and hydrogen-2 ($^2$H).

BACKGROUND OF THE INVENTION

Glycerol is an extremely useful synthon for the synthesis of many important biochemicals and pharmaceuticals. It can be used as a labeling synthon but has limitations. Glycerol has previously been labeled in a variety of ways with $^{13}$C, $^{14}$C and $^2$H. For example, Siskos et al., Tetrahedron Letters, vol. 44, pp. 789-792 (2003) describe the synthesis of [1-$^{13}$C, $^{18}$O] and [1-$^{13}$C, $^2$H$_2$]-glycerol; Barber describes the synthesis of [1-$^{13}$C]-glycerol; and Pitlik et al., J. Labelled Cpd. and Radiopharm., vol. XXXIX, No. 12, pp. 999-1009 (1997) describe the synthesis of $^2$H- and $^{13}$C-labeled glycerols such as [1,1-$^2$H$_2$, 1,2-$^{13}$C]glycerol. Labeled glycerols can be used in the elucidation of biochemical pathways, e.g., Cho et al., J. Org. Chem., vol. 58, pp. 7925-7928 (1993) describe the incorporation of labeled glycerol samples into the mC$_7$N unit of asukamycin. Some labeled glycerols have also been prepared with chirality, e.g., Nieschalk et al., Tetrahedron: Asymmetry, vol. 8, No. 14, pp. 2325-2330 (1997) describe four stereoisomers of [$^2$H]-glycerol; Matteson et al., J. Am. Chem. Soc., vol. 112, 3964-3969 (1990) describe stereoisomers of deuterated glycerol; and Blackmore et al., Journal of Labelled Compounds, vol. 8, no. 1, pp. 71-76 (1972) describe the preparation of L-[1-$^{14}$C]-glycerol.

A new synthon, i.e., labeled glycerol, has now been developed that has the synthetic utility of chirality and allows the differentiation of each of the carbons.

It is an object of the present invention to provide chiral labeled compounds useful for synthetic chemistry development.

SUMMARY OF THE INVENTION

In accordance with the purposes of the present invention, as embodied and broadly described herein, the present invention provides asymmetric chiral labeled glycerols including at least one chiral atom, from one to two $^{13}$C atoms and from zero to four deuterium atoms bonded directly to a carbon atom. Among specific embodiments of the present invention are included:

(2S) [1,2-$^{13}$C$_2$]glycerol, (2R) [1,2-$^{13}$C$_2$]glycerol,

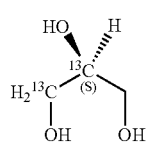 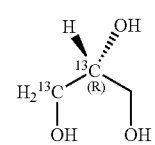

(2S) [1-$^{13}$C, 2-$^2$H]glycerol, (2R) [1-$^{13}$C, 2-$^2$H]glycerol,

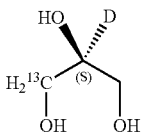 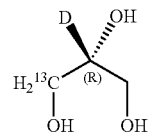

(2S, 3S) [1,2-$^{13}$C$_2$, 3-$^2$H]glycerol, (2R, 3R) [1,2-$^{13}$C$_2$, 3-$^2$H] glycerol, (2S, 3R) [1,2-$^{13}$C$_2$, 3-$^2$H]glycerol, (2R, 3S) [1,2-$^{13}$C$_2$, 3-$^2$H]glycerol,

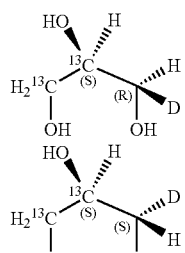 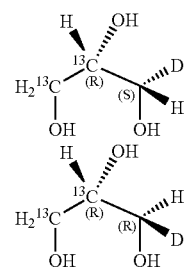

(2S) [1,2-$^{13}$C$_2$, 3-$^2$H]glycerol, (2R) [1,2-$^{13}$C$_2$, 3-$^2$H]glycerol,

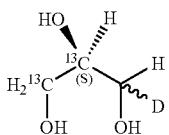 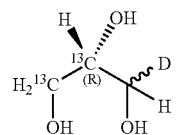

(2S) [1,2-$^{13}$C$_2$, 3-$^2$H$_2$]glycerol, (2R) [1,2-$^{13}$C$_2$, 3-$^2$H$_2$]glycerol,

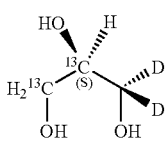 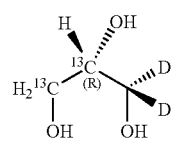

(2S) [1-$^2$H, 2-$^{13}$C]glycerol, (2R) [1-$^2$H, 2-$^{13}$C]glycerol,

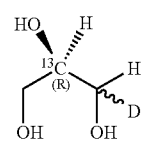 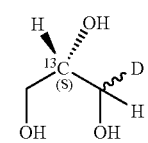

(2S) [1-$^2$H$_2$, 2-$^{13}$C]glycerol, (2R) [1-$^2$H$_2$, 2-$^{13}$C]glycerol,

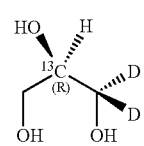 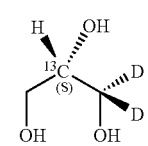

(1S, 2S) [1-$^{13}$C, 1-$^2$H]glycerol, (1R, 2R) [1-$^{13}$C, 1-$^2$H]glycerol, (1S, 2R) [1-$^{13}$C, 1-$^2$H]glycerol, (1R, 2S) [1-$^{13}$C, 1-$^2$H]glycerol,

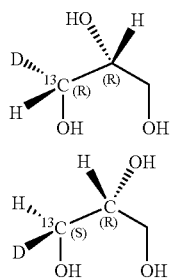
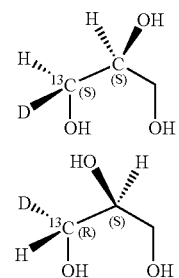

(1R, 2R) [1-$^{13}$C, 1,2-$^2$H$_2$]glycerol, (1S, 2S) [1-$^{13}$C, 1,2-$^2$H$_2$]glycerol, (1R, 2S) [1-$^{13}$C, 1,2-$^2$H$_2$]glycerol,

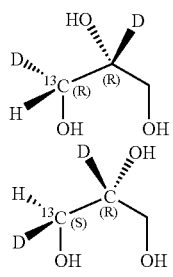
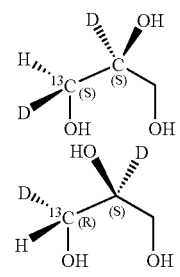

(1R, 2R) [1-$^{13}$C, 1,3-$^2$H$_3$]glycerol, (1S, 2S) [1-$^{13}$C, 1,3-$^2$H$_3$] glycerol, (1S, 2R) [1-$^{13}$C, 1,3-$^2$H$_3$]glycerol, (1R, 2S) [1-$^{13}$C, 1,3-$^2$H$_3$]glycerol,

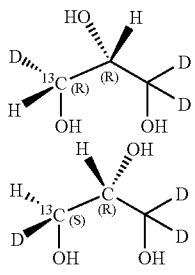
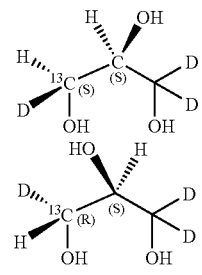

(1R, 2R) [1-$^{13}$C, 1,2,3-$^2$H$_4$]glycerol, (1S, 2S) [1-$^{13}$C, 1,2,3-$^2$H$_4$]glycerol, (1S, 2R) [1-$^{13}$C, 1,2,3-$^2$H$_4$]glycerol, (1R, 2S) [1-$^{13}$C, 1,2,3-$^2$H$_4$]glycerol,

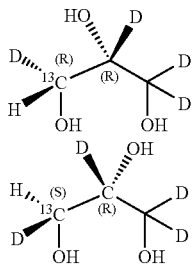
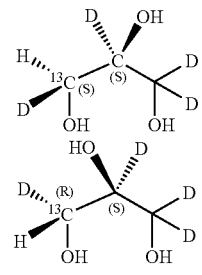

(1R, 2R) [1,2-$^{13}$C$_2$, 1-$^2$H]glycerol, (1S, 2S) [1,2-$^{13}$C$_2$, 1-$^2$H]glycerol, (1S, 2R) [1,2-$^{13}$C$_2$, 1-$^2$H]glycerol, (1R, 2S) [1,2-$^{13}$C$_2$, 1-$^2$H]glycerol,

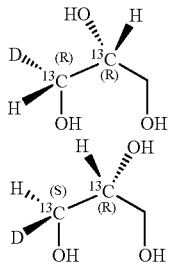
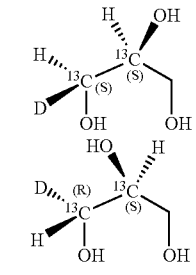

(1R, 2R) [1,2-$^{13}$C$_2$, 1,2-$^2$H$_2$]glycerol, (1S, 2S) [1,2-$^{13}$C$_2$, 1,2-$^2$H$_2$]glycerol, (1S, 2R) [1,2-$^{13}$C$_2$, 1,2-$^2$H$_2$]glycerol, (1R, 2S) [1,2-$^{13}$C$_2$, 1,2-$^2$H$_2$]glycerol,

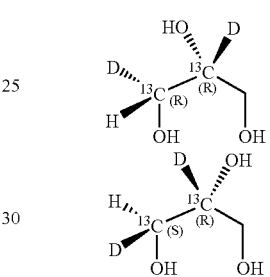
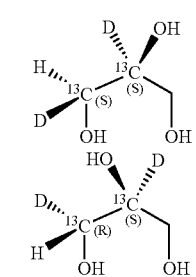

(1R, 2R) [1,2-$^{13}$C$_2$, 1,3-$^2$H$_3$]glycerol, (1S, 2S) [1,2-$^{13}$C$_2$, 1,3-$^2$H$_3$]glycerol, (1S, 2R) [1,2-$^{13}$C$_2$, 1,3-$^2$H$_3$]glycerol, (1R, 2S) [1,2-$^{13}$C$_2$, 1,3-$^2$H$_3$]glycerol,

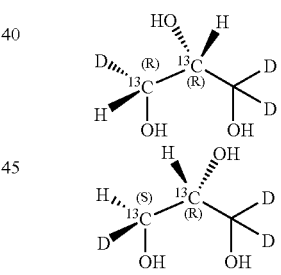
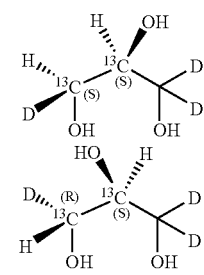

(1R, 2R) [1,2-$^{13}$C$_2$, 1,2,3-$^2$H$_4$]glycerol, (1S, 2S) [1,2-$^{13}$C$_2$, 1,2,3-$^2$H$_4$]glycerol, (1S, 2R) [1,2-$^{13}$C$_2$, 1,2,3-$^2$H$_4$]glycerol, and (1R, 2S) [1,2-$^{13}$C$_2$, 1,2,3-$^2$H$_4$]glycerol

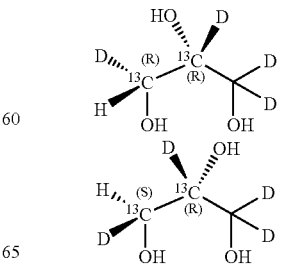
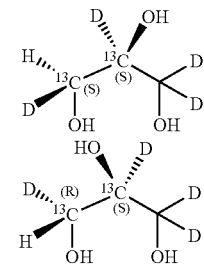

The present invention further provides processes of preparing asymmetric chiral labeled glycerols including at least one chiral atom, from one to two $^{13}$C atoms and from zero to four deuterium atoms bonded directly to a carbon atom.

DETAILED DESCRIPTION

The present invention is concerned with asymmetric chiral labeled compounds, specifically chiral labeled glycerols. Generally, the chiral compounds are labeled with one or two $^{13}$C's, although they may be labeled with up to four deuterium ($^2$H) atoms, i.e., from 0 to 4 $^2$H atoms, as well.

Particularly, the present invention is concerned with the asymmetric chiral labeled glycerols including at least one chiral atom, from one to two $^{13}$C atoms and from zero to two deuterium atoms bonded directly to a carbon atom. Among labeled compounds of the invention are included: (2S) [1,2-$^{13}$C$_2$]glycerol, (2R) [1,2-$^{13}$C$_2$]glycerol, (2S) [1-$^{13}$C, 2-$^2$H]glycerol, (2R) [1-$^{13}$C, 2-$^2$H]glycerol, (2S, 3S) [1,2-$^{13}$C$_2$, 3-$^2$H]glycerol, (2R, 3R) [1,2-$^{13}$C$_2$, 3-$^2$H]glycerol, (2S, 3R) [1,2-$^{13}$C$_2$, 3-$^2$H]glycerol, (2R, 3S) [1,2-$^{13}$C$_2$, 3-$^2$H]glycerol, (2S) [1,2-$^{13}$C$_2$, 3-$^2$H]glycerol, (2R) [1,2-$^{13}$C$_2$, 3-$^2$H]glycerol, (2S) [1,2-$^{13}$C$_2$, 3-$^2$H$_2$]glycerol, (2R) [1,2-$^{13}$C$_2$, 3-$^2$H$_2$]glycerol, (2S) [1-$^2$H, 2-$^{13}$C]glycerol, (2R) [1-$^2$H, 2-$^{13}$C]glycerol, (2S) [1-$^2$H$_2$, 2-$^{13}$C]glycerol, (2R) [1-$^2$H$_2$, 2-$^{13}$C]glycerol, (1S, 2S) [1-$^{13}$C, 1-$^2$H]glycerol, (1R, 2R) [1-$^{13}$C, 1-$^2$H]glycerol, (1S, 2R) [1-$^{13}$C, 1-$^2$H]glycerol, (1R, 2S) [1-$^{13}$C, 1-$^2$H ]glycerol, (1R, 2R) [1-$^{13}$C, 1,2-$^2$H$_2$]glycerol, (1S, 2S) [1-$^{13}$C, 1,2-$^2$H$_2$]glycerol, (1S, 2R) [1-$^{13}$C, 1,2-$^2$H$_2$]glycerol, (1R, 2S) [1-$^{13}$C, 1,2-$^2$H$_2$]glycerol, (1R, 2R) [1-$^{13}$C, 1,3-$^2$H$_3$]glycerol, (1S, 2S) [1-$^{13}$C, 1,3-$^2$H$_3$]glycerol, (1S, 2R) [1-$^{13}$C, 1,3-$^2$H$_3$]glycerol, (1R, 2S) [1-$^{13}$C, 1,3-$^2$H$_3$]glycerol, (1R, 2R) [1-$^{13}$C, 1,2,3-$^2$H$_4$]glycerol, (1S, 2S) [1-$^{13}$C, 1,2,3-$^2$H$_4$]glycerol, (1S, 2R) [1-$^{13}$C, 1,2,3-$^2$H$_4$] glycerol, (1R, 2S) [1-$^{13}$C, 1,2,3-$^2$H$_4$]glycerol, (1R, 2R) [1,2-$^{13}$C$_2$, 1-$^2$H]glycerol, (1S, 2S) [1,2-$^{13}$C$_2$, 1-$^2$H]glycerol, (1S, 2R) [1,2-$^{13}$C$_2$, 1-$^2$H ]glycerol, (1R, 2S) [1,2-$^{13}$C$_2$, 1-$^2$H]glycerol, (1R, 2R) [1,2-$^{13}$C$_2$, 1,2-$^2$H$_2$]glycerol, (1S, 2S) [1,2-$^{13}$C$_2$, 1,2-$^2$H$_2$]glycerol, (1S,2R) [1,2-$^{13}$C$_2$, 1,2-$^2$H$_2$] glycerol, (1R, 2S) [1,2-$^{13}$C$_2$, 1,2-$^2$H$_2$]glycerol, (1R, 2R) [1,2-$^{13}$C$_2$, 1,3-$^2$H$_3$]glycerol, (1S, 2S) [1,2-$^{13}$C$_2$, 1,3-$^2$H$_3$] glycerol, (1S, 2R) [1,2-$^{13}$C$_2$, 1,3-$^2$H$_3$]glycerol, (1R, 2S) [1,2-$^{13}$C$_2$, 1,3-$^2$H$_3$]glycerol, (1R, 2R) [1,2-$^{13}$C$_2$, 1,2,3-$^2$H$_4$] glycerol, (1S, 2S) [1,2-$^{13}$C$_2$, 1,2,3-$^2$H$_4$]glycerol, (1S, 2R) [1,2-$^{13}$C$_2$, 1,2,3-$^2$H$_4$]glycerol, and (1R, 2S) [1,2-$^{13}$C$_2$, 1,2,3-$^2$H$_4$]glycerol.

Among particular labeled compounds are included (2S) [1,2-$^{13}$C$_2$]glycerol and (2R) [1,2-$^{13}$C$_2$]glycerol. (2S) [1,2-$^{13}$C$_2$]glycerol and (2R) [1,2-$^{13}$C$_2$]glycerol are shown in the following structures:

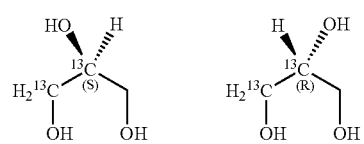

Each of these labeled compounds can be synthesized from a chiral starting material, e.g., (S) or (R) methyl phenyl sulfoxide or analog thereof such as S(−)-methyl p-tolyl sulfoxide and the like.

The reactivity of a labeled acetic acid, (dimethylamino) oxo-, ethyl esters can be tailored to produce a variety of labeled biochemicals and pharmaceuticals with predictable regioselectivity. Preparation of such labeled acetic acid, (dimethylamino)oxo-, ethyl esters is described in U.S. Pat. No. 6,753,446, issued on Jun. 22, 2004 by Martinez et al. for "Synthesis of Labeled Oxalic Acid Derivatives", such description incorporated herein by reference. For example, a general reaction for the production of isotopically labeled glycerol using such a reagent can be as follows.

(S) Methyl phenyl sulfoxide or an analog thereof can be reacted with ethyl N,N-dimethyl [1,2-$^{13}$C] oxamate in THF to form an intermediate product. Such an intermediate product can then be reacted with diisobutylaluminum hydride (DIBAL) followed by reaction with acetic anhydride and sodium acetate and followed by reaction with lithium borohydrate to form a chiral labeled glycerol.

Stable isotope labeled glycerol can be used as the sole source of carbon for the growth of bacteria, which are used to express proteins for structural and mechanistic studies of enzymes carried on in laboratories and required for modern drug development strategies. In addition, labeled glycerols are required for many other phases of drug discovery and development. Most notably, isotopically glycerol is used as a precursor to elucidate biosynthetic pathways of pharmaceutical targets. The natural products labeled specifically from glycerol are required for pharmacokinetics and drug metabolism studies, which are required for the FDA approval process. For many applications, site-specific $^{13}$C or combined $^{13}$C and $^2$H-labeling of glycerol is required. Although glycerol is a symmetric compound, it is acted on by glycerol kinase stereospecifically being phosphorylated specifically on the pro R hydroxymethyl group. Therefore, stereospecifically labeled glycerols may be incorporated specifically into natural products, yielding new and more useful information in all applications of glycerol to label proteins or natural products. For example, it is essential for solution NMR structure studies of proteins to develop a labeling scheme in which a limited number of specific sites in the protein are protonated and $^{13}$C-labeled in an otherwise $^{12}$C-deuterated background. This can be accomplished by labeling the protein with glycerol that is specifically labeled with $^{13}$C and chirally deuterated at the pro R hydroxymethyl. Many of the amino acids derived from (2R, 3S) [1-$^{13}$C, 1-$^2$H]glycerol will be chirally deuterated and labeled with $^{13}$C only in the beta carbon. Symmetrically labeled glycerols have been used extensively for natural product biosynthesis studies. The quality of information about biosynthetic pathways will be greatly enhanced by the stereospecific labeled glycerols described herein.

The present invention is more particularly described in the following examples which are intended as illustrative only, since numerous modifications and variations will be apparent to those skilled in the art.

Synthesis of (2S) [1,2-$^{13}C_2$]glycerol was as outlined below.

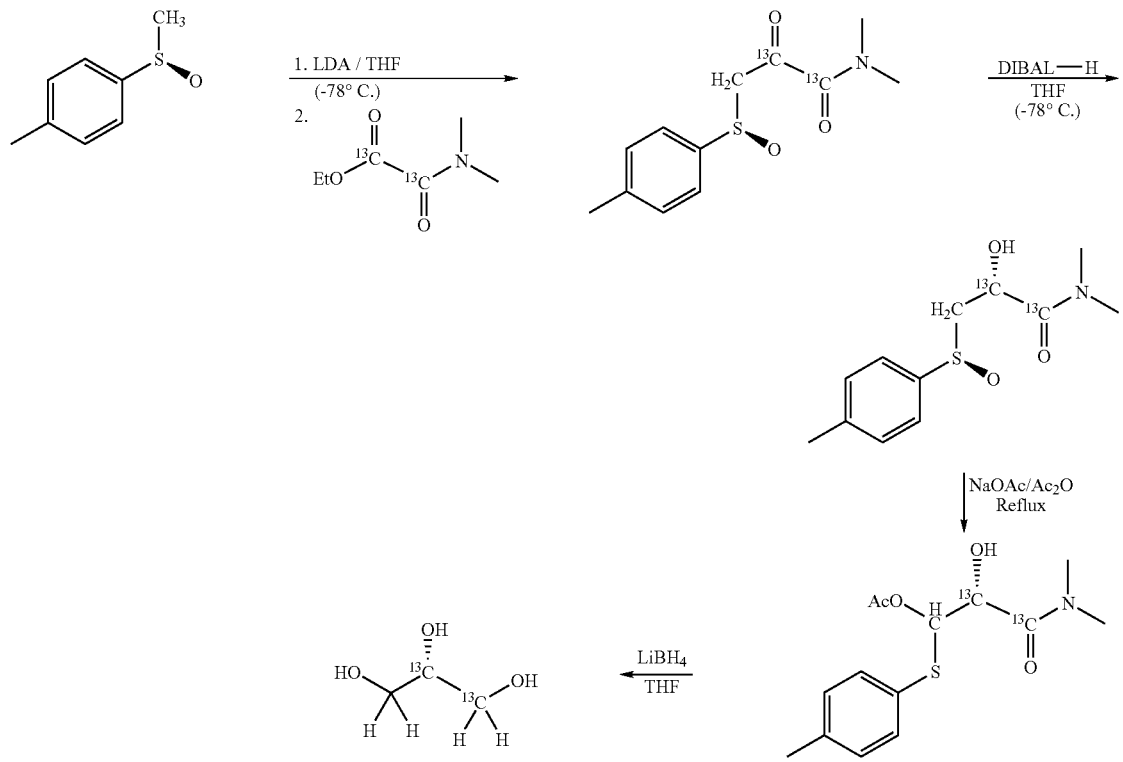

EXAMPLE 1

Synthesis of [2,3-$^{13}C_2$]propanoic acid, 3-[(S)-(4-methylphenyl)sulfinyl]-2-oxo-, diethyl amide was as follows. The S(−)-Methyl p-tolyl sulfoxide (0.98 g, 0.0063 mol) was dissolved in 10 mL of tetrahydrofuran (THF) and cooled to −78° C. To this solution, lithium diisopropyl amide (LDA) (8.5 mL of 1.5M in THF) was added drop wise. After 1 hour a solution of [1,2-$^{13}C_2$]acetic acid, (dimethylamino) oxo-, ethyl ester (0.934 g, 0.875 mL, 0.00635 mole) was added dropwise. The labeled reagent was prepared as described in a manner as described in U.S. patent application Ser. No. 10/456,081, filed on Jun. 5, 2003 by Martinez et al. After 1 hour the reaction was quenched with hydrochloric acid (1M, 30 mL). The mixture was transferred to a separatory funnel and extracted with dichloromethane (4×30 mL). The organic layers were combined and dried over sodium sulfate. Evaporation of the solvent gave 1.77 g of crude product which was purified by column chromatography to give 0.705 g (42.2%) of pure product.

EXAMPLE 2

Reduction of [2,3-$^{13}C_2$]propanoic acid, 3-[(S)-(4-methylphenyl)sulfinyl]-2-oxo-, dimethyl amide was as follows. The [2,3-$^{13}C_2$]propanoic acid, 3-[(S)-(4-methylphenyl)sulfinyl]-2-oxo-, dimethyl amide (0.57 g 0.0022 mol) from example 1 was dissolved in THF (15 mL) and cooled to −78° C. Diisobutyl aluminum hydride (DIBAL), (1.5 mL of 1.0M THF solution) was added dropwise over 5 minutes. The reaction with stirred at this temperature for 2.5 hours. Hydrochloric acid was added and the cold bath was removed. The reaction was allowed to come to room temperature and this mixture was transferred to a separatory funnel. The aqueous portion was extracted with dichloromethane (4×25 mL). The organic layers were combined and dried over sodium sulfate. Removal of the solvent gave 0.628 g of crude product which was used in the subsequent step without purification.

EXAMPLE 3

A pummerer rearrangement of [2,3-$^{13}C_2$]propanoic acid, 2-hydroxy-3-[(R)-(4-methylphenyl)sulfinyl]-, dimethyl amide was as follows. The crude [2,3-$^{13}C_2$]propanoic acid, 2-hydroxy-3-[(R)-(4-methylphenyl) sulfinyl]-, dimethyl amide (0.628 g) from example 2 was dissolved in acetic anhydride (6 mL). Sodium acetate (1.73 g, 0.0021 mole) was added to the solution. The reaction was refluxed for 3 hours. The reaction was allowed to cool to room temperature and toluene (10 mL) was added. The toluene was evaporated and this toluene process was done repeated a total of 4 times. The residue was suspended into dichloromethane (15 mL) and filtered to remove the insoluble sodium acetate. Evaporation of the organic layer gave 0.558 g of crude product. The product was purified by column chromatography.

EXAMPLE 4

Synthesis of (2S) [1,2-$^{13}C_2$]glycerol was as follows. The purified material (0.0597 g, 0.00175 mole) was dissolved in THF (2.5 mL) and cooled to 0° C. To this solution lithium borohydride (0.90 mL, 0.00185 mole) was added and the reaction was allowed to come to room temperature and stirred overnight. The next day an additional 40 equivalents of LiBH$_4$ were added to the reaction and the reaction was stirred for an additional day. The reaction was cooled in an ice bath and to this water (4 mL) was added dropwise. A precipitate formed and that was removed by filtration. The aqueous material was passed through a Dowex column and on evaporation gave the expected product (0.016 g, 99%). The chirality at position-2 was determined as outlined below.

EXAMPLE 5

Reaction of the glycerol from example 4 with Glycerol Kinase gave the products shown below. The reaction products were analyzed by $^{13}$C-NMR and the ratio of glycerol phosphates were (2S) [1,2-$^{13}$C$_2$]glycerol-3-phosphate (92%) and (2R) [1,2-$^{13}$C$_2$]glycerol-3-phosphate (8%).

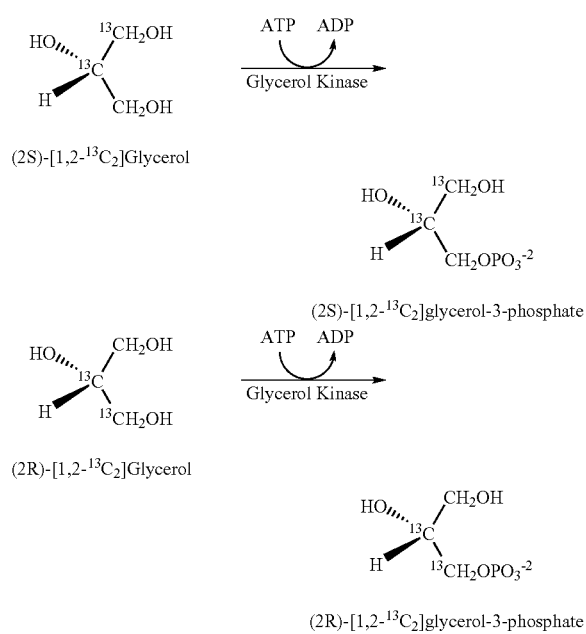

EXAMPLE 6

The (2R) [1,2-$^{13}$C$_2$]glycerol-3-phosphate is produced as the predominate product by starting with R(−)-Methyl p-tolyl sulfoxide in a similar synthesis to examples 1-5 shown above.

Although the present invention has been described with reference to specific details, it is not intended that such details should be regarded as limitations upon the scope of the invention, except as and to the extent that they are included in the accompanying claims.

What is claimed is:

1. An asymmetric chiral labeled glycerol selected from the group consisting of (2S) [2-$^{13}$C]glycerol and (2R) [2-$^{13}$C]glycerol and from one to four deuterium atoms bonded directly to a carbon atom with the proviso that where there is only one deuterium atom, it is bonded to a terminal carbon atom.

2. An asymmetric chiral labeled glycerol selected from the group consisting of (2S) [1,2-$^{13}$C$_2$]glycerol and (2R) [1,2-$^{13}$C$_2$]glycerol and from zero to four deuterium atoms bonded directly to a carbon atom.

3. An asymmetric chiral labeled glycerol selected from the group consisting of (2S, 3S) [1,2-$^{13}$C$_2$, 3-$^2$H]glycerol, (2R, 3R) [1,2-$^{13}$C$_2$, 3-$^2$H]glycerol, (2S, 3R) [1,2-$^{13}$C$_2$, 3-$^2$H]glycerol, (2R, 3S) [1,2-$^{13}$C$_2$, 3-$^2$H]glycerol, (2S) [1-$^{13}$C, 2-$^2$H]glycerol and (2R) [1-$^{13}$C, 2-$^2$H]glycerol.

4. The asymmetric chiral labeled glycerol of claim 2 wherein said glycerol is selected from the group consisting of (2S) [1,2-$^{13}$C$_2$, 3-$^2$H]glycerol and (2R) [1,2-$^{13}$C$_2$, 3-$^2$H]glycerol.

5. The asymmetric chiral labeled glycerol of claim 2 wherein said glycerol is selected from the group consisting of (2S) [1,2-$^{13}$C$_2$, 3-$^2$H$_2$]glycerol and (2R) [1,2-$^{13}$C$_2$, 3-$^2$H$_2$]glycerol.

6. The asymmetric chiral labeled glycerol of claim 1 wherein said glycerol is selected from the group consisting of (2S) [1-$^2$H, 2-$^{13}$C]glycerol and (2R) [1-$^2$H, 2-$^{13}$C]glycerol.

7. The asymmetric chiral labeled glycerol of claim 1 wherein said glycerol is selected from the group consisting of (2S) [1-$^2$H$_2$, 2-$^{13}$C]glycerol and (2R) [1-$^2$H$_2$, 2-$^{13}$C]glycerol.

8. An asymmetric chiral labeled glycerol selected from the group consisting of (1S, 2S) [1-$^{13}$C, 1-$^2$H]glycerol, (1R, 2R) [1-$^{13}$C, 1-$^2$H]glycerol, (1S, 2R) [1-$^{13}$C, 1-$^2$H]glycerol and (1R, 2S) [1-$^{13}$C, 1-$^2$H]glycerol.

9. An asymmetric chiral labeled glycerol including two chiral atoms, from one to two $^{13}$C atoms and from one to four deuterium atoms bonded directly to a carbon atom.

10. The asymmetric chiral labeled glycerol of claim 9 wherein said glycerol is selected from the group consisting of
(1R, 2R) [1-$^{13}$C, 1,2-$^2$H$_2$]glycerol, (1S, 2S) [1-$^{13}$C, 1,2-$^2$H$_2$]glycerol,
(1S, 2R) [1-$^{13}$C, 1,2-$^2$H$_2$]glycerol, (1R, 2S) [1-$^{13}$C, 1,2-$^2$H$_2$]glycerol,
(1R, 2R) [1-$^{13}$C, 1,3-$^2$H$_3$]glycerol, (1S, 2S) [1-$^{13}$C, 1,3-$^2$H$_3$]glycerol,
(1S, 2R) [1-$^{13}$C, 1,3-$^2$H$_3$]glycerol and (1R, 2S) [1-$^{13}$C, 1,3-$^2$H$_3$]glycerol.

11. The asymmetric chiral labeled glycerol of claim 9 wherein said glycerol is selected from the group consisting of
(1R, 2R) [1-$^{13}$C, 1,2,3,3-$^2$H$_4$]glycerol, (1S, 2S) [1-$^{13}$C, 1,2,3,3-$^2$H$_4$]glycerol,
(1S, 2R) [1-$^{13}$C, 1,2,3,3-$^2$H$_4$]glycerol and (1R, 2S) [1-$^{13}$C, 1,2,3,3-$^2$H$_4$]glycerol.

12. The asymmetric chiral labeled glycerol of claim 9 wherein said glycerol is selected from the group consisting of
(1R, 2R) [1,2-$^{13}$C$_2$, 1-$^2$H]glycerol, (1S, 2S) [1,2-$^{13}$C$_2$, 1-$^2$H]glycerol,
(1S, 2R) [1,2-$^{13}$C$_2$, 1-$^2$H]glycerol and (1R, 2S) [1,2-$^{13}$C$_2$, 1-$^2$H]glycerol.

13. The asymmetric chiral labeled glycerol of claim 9 wherein said glycerol is selected from the group consisting of
(1R, 2R) [1,2-$^{13}$C$_2$, 1,2-$^2$H$_2$]glycerol, (1S, 2S) [1,2-$^{13}$C$_2$, 1,2-$^2$H$_2$]glycerol,
(1S, 2R) [1,2-$^{13}$C$_2$, 1,2-$^2$H$_2$]glycerol and (1R, 2S) [1,2-$^{13}$C$_2$, 1,2-$^2$H$_2$]glycerol.

14. The asymmetric chiral labeled glycerol of claim 9 wherein said glycerol is selected from the group consisting of
(1R, 2R) [1,2-$^{13}$C$_2$, 1,3-$^2$H$_3$]glycerol, (1S, 2S) [1,2-$^{13}$C$_2$, 1,3-$^2$H$_3$]glycerol,
(1S, 2R) [1,2-$^{13}$C$_2$, 1,3-$^2$H$_3$]glycerol and (1R, 2S) [1,2-$^{13}$C$_2$, 1,3-$^2$H$_3$]glycerol.

15. The asymmetric chiral labeled glycerol of claim 9 wherein said glycerol is selected from the group consisting of (1R, 2R) [1,2-$^{13}C_2$, 1,2,3,3-$^2H_4$]glycerol, (1S, 2S) [1,2-$^{13}C_2$, 1,2,3,3-$^2H_4$]glycerol, (1S, 2R) [1,2-$^{13}C_2$, 1,2,3,3-$^2H_4$]glycerol and (1R, 2S) [1,2-$^{13}C_2$, 1,2,3,3-$^2H_4$]glycerol.

* * * * *